United States Patent [19]
Brody

[11] Patent Number: 5,542,415
[45] Date of Patent: Aug. 6, 1996

[54] APPARATUS AND PROCESS FOR CONTROLLING THE VENTILATION OF THE LUNGS OF A PATIENT

[75] Inventor: Michael P. Brody, LaMesa, Calif.

[73] Assignee: Infrasonics, Inc., San Diego, Calif.

[21] Appl. No.: 696,582

[22] Filed: May 7, 1991

[51] Int. Cl.⁶ .......................... A61M 16/00; A62B 7/00; F16K 31/02
[52] U.S. Cl. ................... 128/204.23; 128/204.21
[58] Field of Search .................. 128/204.21, 204.23, 128/204.26, 721, 722, 639, 640, 671, 716

[56] References Cited

U.S. PATENT DOCUMENTS

| | | | |
|---|---|---|---|
| 3,985,131 | 10/1976 | Buck et al. | 128/204.23 |
| 4,256,101 | 3/1981 | Ellestad et al. | 128/204.23 |
| 4,357,936 | 11/1982 | Ellestad et al. | 128/204.23 |
| 4,433,693 | 2/1984 | Hochstein | 128/721 |
| 4,444,201 | 4/1984 | Itoh | 128/204.23 |
| 4,648,395 | 3/1987 | Sato et al. | 128/204.23 |
| 4,696,307 | 9/1987 | Montgieux | 128/721 |
| 4,813,427 | 3/1989 | Schlaefke et al. | 128/721 |
| 4,895,160 | 1/1990 | Reents | 128/671 |
| 4,915,103 | 4/1990 | Visveshwara et al. | 128/204.23 |
| 5,099,836 | 3/1992 | Rowland et al. | 128/204.23 |

OTHER PUBLICATIONS

Short, *Microprocessors and Programmed Logic*, pp. 16 & 19, Prentice–Hall, Inc., Englewood Cliffs, NJ, © 1981. ISBN 0-13-581173-2.

Visveshwara et al, *Patient–Triggered Synchronized Ventilation of Newborns*, Jnl of Perinatology, vol. XI, No. 4, 1991, pp. 347–354.

*Primary Examiner*—Kimberly L. Asher
*Attorney, Agent, or Firm*—Gregory Garmong

[57] ABSTRACT

The breathing of a patient is monitored with a movement sensor, taped to the abdomen of the patient, that produces an output signal indicative of the movement of the diaphragm of the patient. The rate of change of the output signal with time is determined. When the rate of change with time exceeds a preselected value, a ventilation of the lungs of the patient by an external ventilator is initiated.

15 Claims, 3 Drawing Sheets

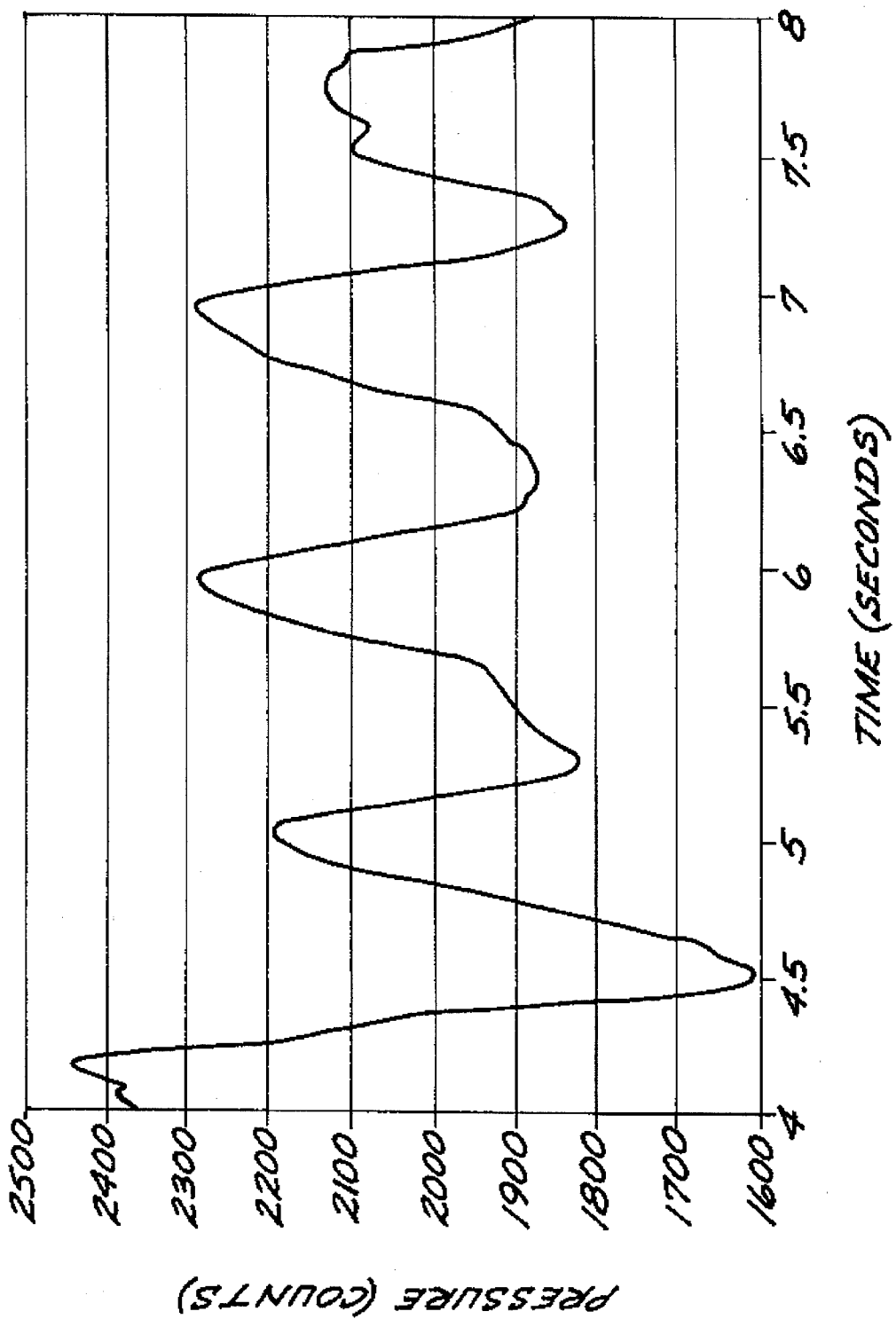

APPARATUS AND PROCESS FOR CONTROLLING THE VENTILATION OF THE LUNGS OF A PATIENT

BACKGROUND OF THE INVENTION

This invention relates to techniques for assisting patients to breathe, and, more particularly, to an approach for synchronizing an external ventilator to the spontaneous breathing of the patient.

Undersized and premature infants, as well as full-term infants, often have difficulty breathing. The inability to breath regularly results in insufficient aeration of the blood of the baby, in turn leading to or exacerbating other problems. As with breathing disorders in older persons, the infant may devote such a large amount of its energy to breathing that it cannot overcome infections and disorders.

It is sometimes observed that the infant's condition can be remarkably improved simply by ensuring a regular air supply that permits its energy to be directed elsewhere. Most undersized and premature babies are therefore placed onto a program of breathing assistance with a device termed a "ventilator". In simplest terms, the ventilator either forces pressurized gas into the lungs (e.g., a positive-pressure ventilator) or expands the chest cavity to draw gas into the lungs (e.g., a negative-pressure ventilator such as an iron lung) under a selectable schedule of gas composition, pressure, and flow pattern.

While negative-pressure ventilators enjoyed a degree of popularity in the past, their use has been largely replaced by positive-pressure ventilators. The positive-pressure ventilator is a mechanical device external to the patient, which creates an external pressure and thereby forces gas into the patient's lungs through a tube, termed the airway. The gas may be air, pure oxygen, air enriched with additional oxygen, or some other oxygen-containing mixture.

The ventilator can operate in several different modes. In one, the ventilator introduces gas into the lungs of the patient on a regular basis, without any effort by the patient. (As used herein, a "breath" is an inhalation of gas made by the patient with its own efforts, while "ventilation" is the introduction of gas into the lungs that can occur either due to a breath, or in the absence of a breath by the operation of the ventilator.) In another mode of operation, the patient does breathe, but the ventilator supplies additional gas to that which the patient could itself bring into its lungs, or the ventilator supplies intermediate ventilations in addition to those made by the patient with its own efforts.

In another mode of operation, the operation of the ventilator is synchronized to the breathing of the patient, so that the ventilator is not forcing gas into the lungs at the same time that the patient is attempting to breathe out. The present invention is concerned with the control of the ventilator so that it is synchronized with the breathing efforts of the patient.

The present invention finds its greatest application to infant patients because of their special requirements, but is also useful for other patients with specialized breathing problems. The breathing of undersized and premature infants differs from that of adults in at least two important respects. Infants generally breathe much faster than do adults. Infants typically breathe at a rate of 30 or more breaths per minute and often breathe at irregular intervals, while adults at rest typically breathe about 15 times per minute in regular intervals. The inspiration time required to draw the breath into the lungs is typically about 200-400 milliseconds (0.2-0.4 seconds) for an infant. Second, the lungs of the infant are much smaller than those of the adult, so that the volume of gas inhaled and exhaled during a breath, and the pressure within the lungs, are smaller than those of the adult.

Synchronization of the ventilator to the breathing of infants is therefore much more difficult than similar synchronization to adults, because it is difficult to determine when the baby breathes and because the reaction of the ventilator must be very fast once the initiation of a breath is detected. Studies have indicated that the ventilator must start its ventilation within some short time interval, typically about 60 milliseconds or less, after the baby begins its voluntary breath, or the ventilator may provide little assistance or may actually end up working against the infant's own efforts.

Adult ventilators are typically synchronized with the adult's own breathing by placing a proximal pressure sensor in the airway of the ventilator just outside the patient. A sufficiently lower pressure in the airway, relative to the positive end expiratory pressure (PEEP), is then interpreted as a breath. Because of the relatively slow, regular breathing and relatively large pressure changes, the initiation of the breath is readily determined.

The use of such a technique for an infant is not practicable for the reasons indicated. In another approach under study for infants, a sensor that measures the movement of the abdomen of the infant is used to trigger ventilator operation when the movement exceeds a selected value. Studies with this approach have obtained triggering within about 110–120 milliseconds of the spontaneous initiation of the breath, but have not attained initiation within the desired 60 milliseconds. With triggering at 110–120 milliseconds, the inhalation of gas by the baby is about ⅔ complete before the ventilator begins to provide any assistance. It is therefore now common practice not to use a synchronized breathing mode for ventilation of undersized and premature infants, because no generally satisfactory synchronization approach exists.

There exists a need for a better approach to the synchronization of a ventilator to a patient's own breathing, particularly for infant patients. Such an improved approach would significantly improve the potential for respiratory care of the patients. The present invention fulfills this need, and further provides related advantages.

SUMMARY OF THE INVENTION

The present invention provides an approach for controlling a ventilator that permits mechanical ventilation to be closely synchronized with the patient's spontaneous breathing. The technique of the invention measures the patient's own efforts to breathe using a noninvasive sensor and initiates ventilator operation within a short time, typically about 60 milliseconds or less of the beginning of the patient's own effort to breathe. The ventilator is therefore able to assist the breathing for a large part of the inspiration phase of the spontaneous breath.

In accordance with the invention, apparatus for controlling the ventilation of a patient by a ventilator device comprises means for determining the movement of an patient's diaphragm, the means including a sensor that contacts the external portion of the abdomen of the patient and produces a signal responsive to the movement of the diaphragm of the patient, means for determining the rate of change of the sensor signal with time, and means for controlling a ventilator based upon the rate of change of the sensor signal with time.

More specifically and in relation to a preferred embodiment, apparatus for controlling the ventilation of a patient by a ventilator device comprises a compressible sensor fastened to an patient's abdomen, the compressible sensor producing a pressure output related to the movement of the abdomen of the patient. A pressure transducer receives the pressure output of the sensor and produces a transducer electrical output related thereto. An electronic circuit controls a ventilator based upon the rate of change with time of the transducer output.

The apparatus of the invention is preferably implemented with a sensor having a sealed chamber taped to the abdomen of the patient. When an infant breathes spontaneously, its diaphragm moves down and its chest wall collapses. The abdomen compresses, causing an abdominal expansion that compresses the gas within the interior of the sensor taped to the abdomen. A pressure transducer communicating with the interior of the sensor monitors the gas pressure as a function of time, and produces an electrical output signal proportional thereto. The time rate of change of the transducer signal is calculated and, when that rate of change exceeds a preselected value, the mechanical ventilator is triggered. The time rate of change of pressure can also be used to determine inspiration time and breath rate, and monitor the patient for apnea (discontinuance of breathing).

The present invention provides an important advance in the art of patient ventilation, particularly for infants. Testing has demonstrated that ventilator inspiration can be initiated within a required short time, typically 60 milliseconds or less, from the start of the spontaneous breath, so that the ventilator can provide assistance over a large fraction of the inspiration phase. Other features and advantages of the invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 5 is a graph of pressure as a function of time for an infant breathing.

DETAILED DESCRIPTION OF THE PREFERRED EMBODIMENT

In accordance with a preferred embodiment of the invention, apparatus for controlling the ventilation of a patient includes a compressible sensor adapted for fastening to a patient's abdomen, the compressible sensor producing a pressure output related to the compression of the sensor. A pressure transducer receives the pressure output of the sensor and produces a transducer electrical output related thereto. A means for initiating a ventilation of the patient's airways functions when the rate of change of transducer electrical output with time exceeds a preselected value.

Figure 1:
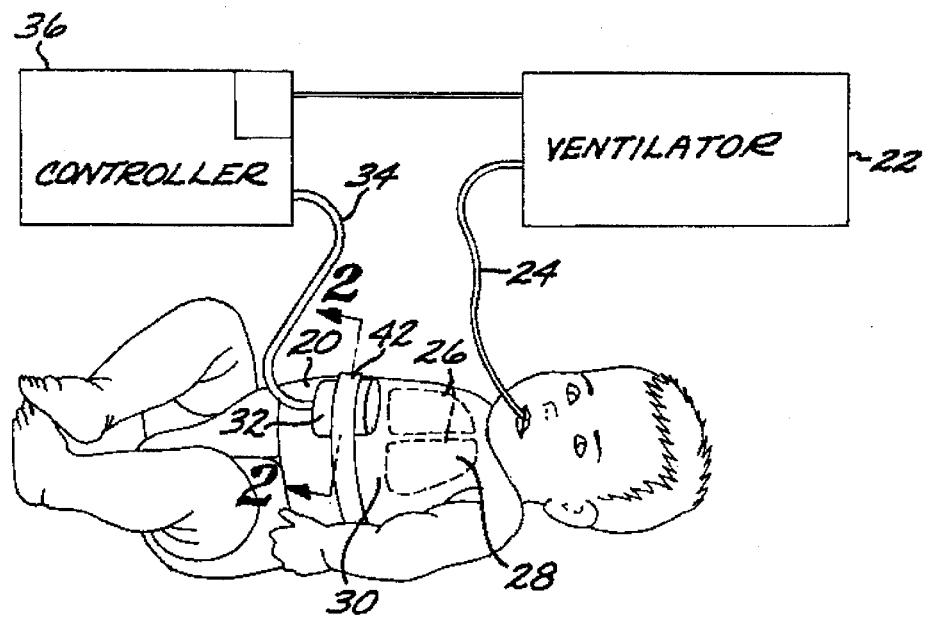
FIG. 1 is a schematic view of the apparatus of the invention in relation to an infant and the ventilator.

FIG. 1 illustrates an infant 20 undergoing ventilation by a ventilator 22. The ventilator 22 forces pressurized gas through an airway 24 into the infant's lungs 26 through its nose or mouth. The ventilator 22 is not itself part of the present invention, and may be any acceptable type. A preferred ventilator 22 is manufactured by Infrasonics, Inc., San Diego, Calif. and sold under the trademark INFANT STAR.

When the infant 20 attempts to breathe by its own effort, its chest cavity 28 contracts and its abdomen 30 expands. The movement of the abdomen 30 is detected by a sensor 32 taped to the abdomen of the infant 20. A pressure communication tube 34 extends from the interior of the sensor 32 to a controller 36.

Figure 2:
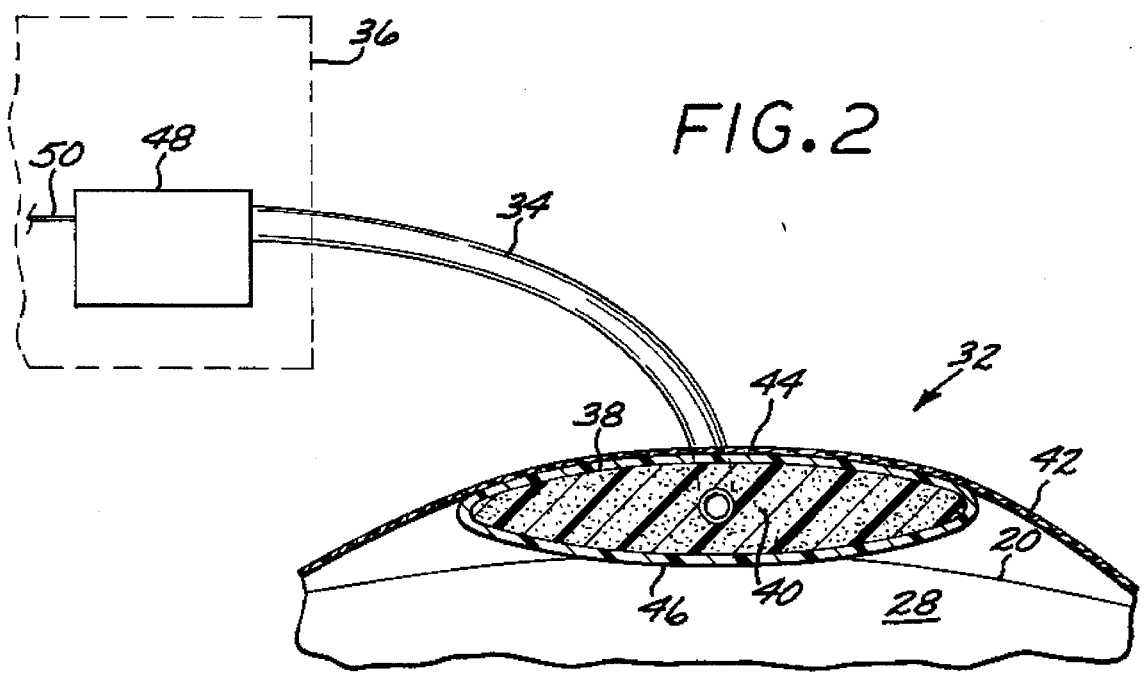
FIG. 2 is a side sectional view of the sensor.

The sensor 32 is illustrated in more detail in FIG. 2. The sensor is formed as a sealed plastic envelope 38 containing a plastic foam 40. The communication tube 34 communicates with the interior of the envelope 36. The sensor 32 is fastened with a piece of tape 42 to the abdomen of the infant 20, in the manner indicated in FIG. 1.

The piece of tape 42 holds an upper surface 44 of the sensor envelope 38 in a relatively fixed position in respect to the vertical movement of the abdomen of the infant. As the abdomen of the infant expands during a breath, a lower surface 46 of the envelope 38 moves upwardly, reducing the volume within the interior of the envelope 38. The pressure within the communication tube 34 increases, and that pressure increase is monitored by a pressure transducer 48 in the controller 36. The transducer 48 produces an electrical signal 50 proportional to the pressure. Suitable sensors, communication tubes, and transducers are known in the art and available commercially. The construction of such a sensor is described in European Patent Specification 0 019 321B, issued May 11, 1983, whose disclosure is incorporated by reference.

Figure 3:
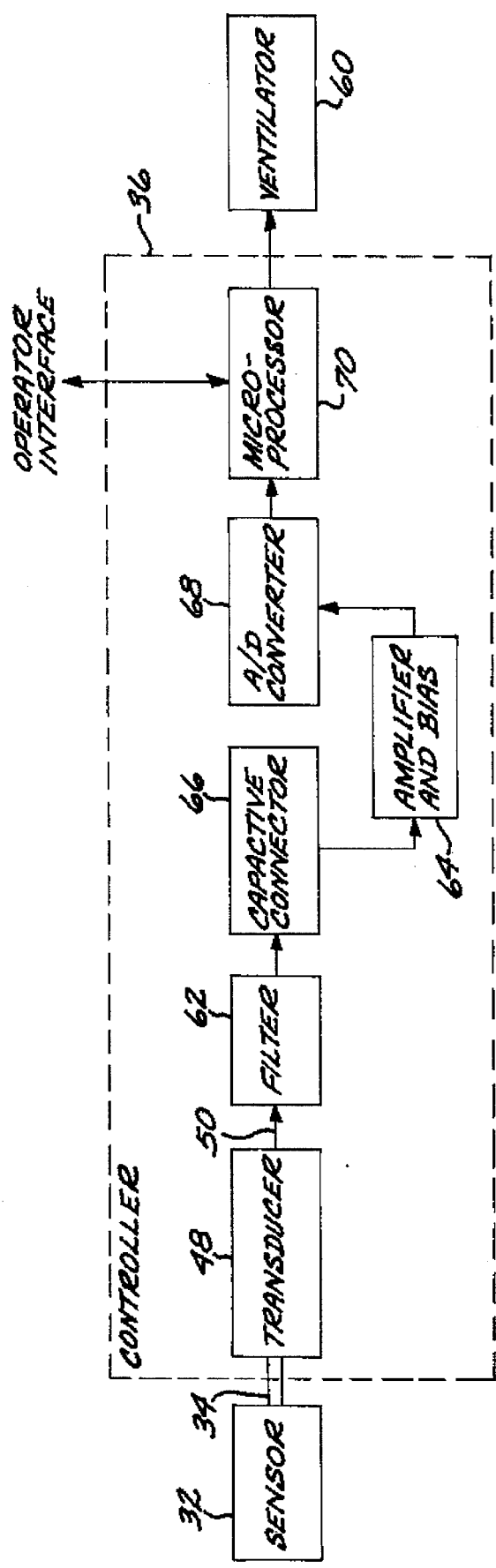
FIG. 3 is a schematic drawing of the electronic circuitry used to analyze the infant chest movement.

FIG. 3 presents a block diagram for the electrical circuitry used to trigger the ventilator 22 based upon the measurements of the transducer 48. The electrical signal 50 is first filtered by a band-pass filter 62 to remove unwanted noise and the initial voltage levels. In the preferred embodiment, the pass band of the filter 62 is from about 0.6 Hz to about 3.4 Hz (3 dB). The output of the filter 62 is coupled to an amplifier 64 through a capacitor 66. The capacitive coupling of the filter output blocks the bias voltage produced by the initial pressure on the sensor. The gain of the amplifier 64 may therefore be selected to be quite high without the initial pressure exceeding the voltage range of the circuit.

The amplifier 64 amplifies and biases its input to the center of a selected voltage range. For example, the output signal of the amplifier 64 may be selected to be at the midpoint of a 0–5 volt range when there is no change in pressure, permitting subsequent analysis of both positive and negative pressure changes. The analog output voltage of the amplifier 54 is converted to a digital value by an analog-to-digital converter 68. In the preferred embodiment, the analog output range of the amplifier 64 is 0–5 volts. The A/D converter 68 divides this voltage range into 4095 equal parts, so that each digital count corresponds to 1.22 millivolts. The output of the amplifier 64 is converted to a digital signal to permit digital processing by a microprocessor 70, which, after analysis of the pressure signal, controllably triggers the ventilator 22.

The microprocessor 70 continuously samples the digital output of the A/D converter 68, and then averages the sampled data obtained over a fixed time period. In a preferred embodiment, the A/D converter 68 output is sampled 8 times over a 5 millisecond period and averaged to reduce the influence of random noise that may have passed through the analog filter 62. The microprocessor 70 then subtracts from the current averaged digital output signal the averaged digital output signal obtained in the prior 5 millisecond period, after correcting for capacitive drift. The result is a change of voltage per 5 millisecond interval, or a rate of change of voltage.

Figure 4:
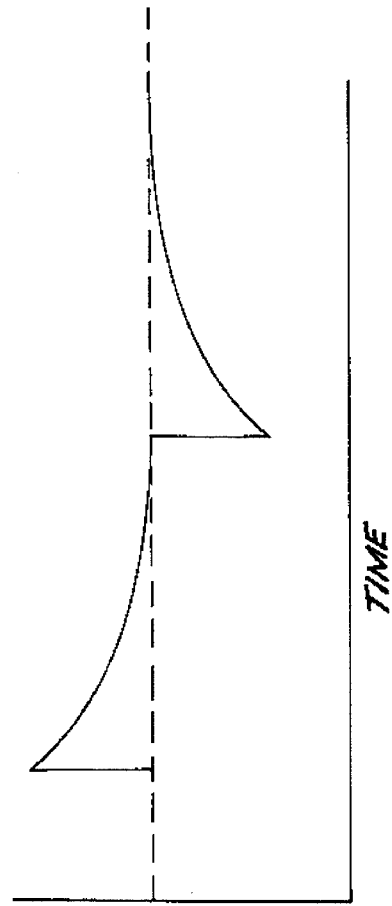
FIG. 4 is a graph of measured instrument voltage decay as a function of time.

The total voltage signal includes that due to the movement of the patient's abdominal wall, and also due to capacitive decay or drift. Because of the capacitive coupling at the capacitor 66, there is a decay toward the mid-point of the voltage range that naturally occurs regardless of patient movement, as shown in FIG. 4. Thus, the total voltage change in 5 milliseconds is the sum of the voltage change resulting from patient abdominal movement and the voltage change resulting from capacitive drift. The voltage change resulting from patient abdominal movement is the quantity of interest, and it is determined by subtracting from the total voltage change the voltage change resulting from capacitive drift. The voltage change resulting from capacitive decay is a function of the RC time constant of the electrical circuit. It can be measured by suddenly increasing or decreasing the pressure on the sensor and then holding the pressure constant, while monitoring the voltage at the A/D converter 68, as illustrated in FIG. 4. At an initial time $t_o$ the sensor pressure is suddenly increased then held constant until $t_1$ when the pressure is suddenly decreased then held constant. During the hold period, the voltage returns to its bias position almost exponentially. This rate of decay or drift is a function of the RC time constant of the electrical circuit. In the presently preferred approach, the voltage drift is measured during calibration of the instrument and stored in a look-up table within the microprocessor 70. Correction of the voltage is accomplished by looking up the 5-millisecond voltage drift at the location in the table corresponding to the total voltage, and then subtracting that voltage drift from the total voltage change during the 5 millisecond interval to obtain the voltage change due to patient abdominal movement.

The voltage change due to patient abdominal movement is used to determine the change in breathing mode of the patient. If the patient is expiring (breathing out), the onset of inspiration (breathing in) is determined as a positive voltage change of more than some preselected amount (inspiration trigger level). For typical situations of infant breathing, an inspiration trigger level of 4 digital counts (4.88 millivolts) has been found acceptable. For optimum results, the microprocessor 70 adjusts the trigger level automatically depending on the strength of the pressure signal. Conversely, if the patient is inspiring, the onset of expiration is determined as a negative voltage change of more than some preselected amount (expiration trigger level). For typical situations of infant breathing, an expiration trigger level of 4 digital counts, has been found acceptable, but again the trigger level may be adjusted.

The determination of the onset of inspiration or expiration is used by the microprocessor 70 to command the ventilator 22 to assist in the breathing. The nature of the breathing assistance is determined by the protocol established by the doctor overseeing the patient. Generally, however, when the onset of inspiration is detected, the ventilator 22 increases the airway pressure for a preselected amount of time. Thus, the ventilator quickly responds to the patient's own efforts to breathe and assists the patient in accomplishing the breathing.

FIG. 5 is a measured graph of the voltage produced by a pressure sensor attached to an infant. The microprocessor reads this voltage every 5 milliseconds, and then subtracts out the voltage change due to capacitive drift. It then compares this voltage change to predetermined trigger levels to decide whether or not to trigger a ventilator breath.

The present invention thus provides an important advance in the art of controlling ventilation, particularly for infants. Although particular embodiments of the invention have been described in detail for purposes of illustration, various modifications may be made without departing from the spirit and scope of the invention. Accordingly, the invention is not to be limited except as by the appended claims.

What is claimed is:

1. Apparatus for controlling the ventilation of a patient by a ventilator, comprising:

means for determining the movement of a patient's diaphragm, said means including a sensor adapted for contacting to the external portion of the abdomen of the patient that produces a signal responsive to the movement of the diaphragm of the patient;

means for determining the rate of change of the sensor signal with time; and means for controlling a ventilator based upon the rate of change of the sensor signal with time.

2. The apparatus of claim 1, wherein the sensor includes a compressible envelope.

3. The apparatus of claim 1, wherein the sensor is a pressure sensor that produces a pressure output signal responsive to the movement of a surface to which it is attached, and the means for determining includes a pressure transducer that produces an electrical output signal responsive to the pressure output of the pressure sensor.

4. The apparatus of claim 1, wherein the sensor produces an electrical output signal.

5. The apparatus of claim 4, wherein the means for controlling includes a filter that receives the electrical output signal and filters out noise from the electrical output signal, an amplifier that amplifies and biases the output signal from the filter, a capacitive coupler between the filter and the amplifier, an analog-to-digital converter that produces a digital signal level responsive to the output signal from the amplifier, and a microprocessor that analyzes the digital signal level produced by the analog-to-digital converter.

6. The apparatus of claim 5, wherein the microprocessor contains means for compensating for capacitive drift in the digital signal level resulting from the capacitive coupler.

7. Apparatus for controlling the ventilation of a patient, comprising:

a sensor that produces a pressure output signal responsive to the movement of a surface to which it is affixed;

a pressure transducer that receives the pressure output signal of the sensor and produces a transducer electrical output signal related thereto; and means for initiating a ventilation of the patient when the rate of change of transducer electrical output signal with time exceeds a preselected value.

8. The apparatus of claim 7, wherein the sensor includes a compressible envelope adapted to be fastened to a patient's abdomen, the compressible sensor producing a pressure output related to the movement of the abdomen of the patient.

9. The apparatus of claim 8, wherein the compressible envelope is made of plastic and is filled with a compressible foam.

10. The apparatus of claim 9, wherein the means for initiating includes a filter that receives the electrical output signal and filters out noise from the electrical output signal, an amplifier that amplifies and biases the output signal from the filter, a capacitive coupler between the filter and the amplifier, an analog-to-digital converter that produces a digital signal level responsive to the output signal from the amplifier, and a microprocessor that analyzes the digital signal level produced by the analog-to-digital converter.

11. The apparatus of claim 10, wherein the microprocessor includes means for compensating the digital signal for capacitive drift in the digital signal level resulting from the capacitive coupler.

12. The apparatus of claim 10, wherein the microprocessor includes means for comparing the digital signal with a preselected trigger level for initiating operation of the ventilator.

13. A process for controlling the ventilation of a patient, comprising:

fixing a sensor that produces a pressure output signal responsive to the movement of a surface to which it is affixed to the external surface of the abdomen of a patient;

providing the pressure output signal of the sensor to a pressure transducer that receives the pressure output signal of the sensor and produces a transducer electrical output signal related thereto; and initiating a ventilation of the patient when the rate of change of transducer electrical output signal with time exceeds a preselected value.

14. The process of claim 13, wherein the sensor includes a compressible envelope adapted to be fastened to the patient's abdomen, the compressible sensor producing a pressure output related to the movement of the abdomen of the patient.

15. The process of claim 14, wherein the compressible envelope is made of plastic and is filled with a compressible foam.

\* \* \* \* \*